United States Patent [19]

Pfohl

[11] Patent Number: 4,705,048
[45] Date of Patent: Nov. 10, 1987

[54] VITAL SIGNS MONITORING SYSTEM

[75] Inventor: Robert L. Pfohl, Anaheim Hills, Calif.

[73] Assignee: Vitacomm, Ltd., Orange, Calif.

[21] Appl. No.: 827,777

[22] Filed: Feb. 7, 1986

Related U.S. Application Data

[63] Continuation of Ser. No. 660,454, Oct. 12, 1984, abandoned, which is a continuation-in-part of Ser. No. 522,640, Aug. 11, 1983, Pat. No. 4,619,268.

[51] Int. Cl.$^4$ .................................................. A61B 7/00
[52] U.S. Cl. .................................... 128/715; 128/773; 128/908
[58] Field of Search ............... 128/668, 670, 680, 687, 128/689, 700, 709, 715, 736, 773, 774, 904, 908

[56] References Cited

U.S. PATENT DOCUMENTS

| | | | |
|---|---|---|---|
| 3,182,129 | 5/1965 | Clark et al. | 128/715 |
| 3,488,586 | 1/1970 | Watrous et al. | 128/908 |
| 4,141,350 | 2/1979 | Shinoda | 128/680 |
| 4,248,241 | 2/1981 | Tacchi | 128/715 |
| 4,308,870 | 1/1982 | Arkans | 128/736 |

*Primary Examiner*—William E. Kamm
*Attorney, Agent, or Firm*—Baker, Maxham & Jester

[57] ABSTRACT

A vital signal monitoring system for monitoring the vital signs of a patient, particularly prior to and during anesthesiology, during and after operational procedures, includes first sensor unit including a microphone for mounting on the patient's chest for picking up breath and heart sounds with a filter and automatic gain control circuit, second sensor unit including a microphone for positioning beneath the blood pressure cuff for picking up the blood flow sounds with a filter and automatic gain control circuit, both connected into a system of electronic components with selection means for selecting either of these sound systems and transmitting the sounds by way of an audio IR transmitter to a portable audio IR receiver carried by a monitoring physician, including an earphone for monitoring the selected sounds. Each sensor unit also includes a thermnistor for measuring the patient's external temperature. This system is combined into a patient monitoring system including an esophageal stethoscope for monitoring a patient's vital signs during surgery with the system including electronics processing circuitry and a microprocessor unit programmed to initiate test procedures, control multiple vital signsl displays and for initiating one or more alarms in response to deviation from normal vital signs conditions. The overall system includes a switch selector bank permitting the monitoring physician to select one of the three sensing systems to monitor with the portable receiver enabling the attending physician to move freely about an operating room during the monitoring procedures.

12 Claims, 6 Drawing Figures

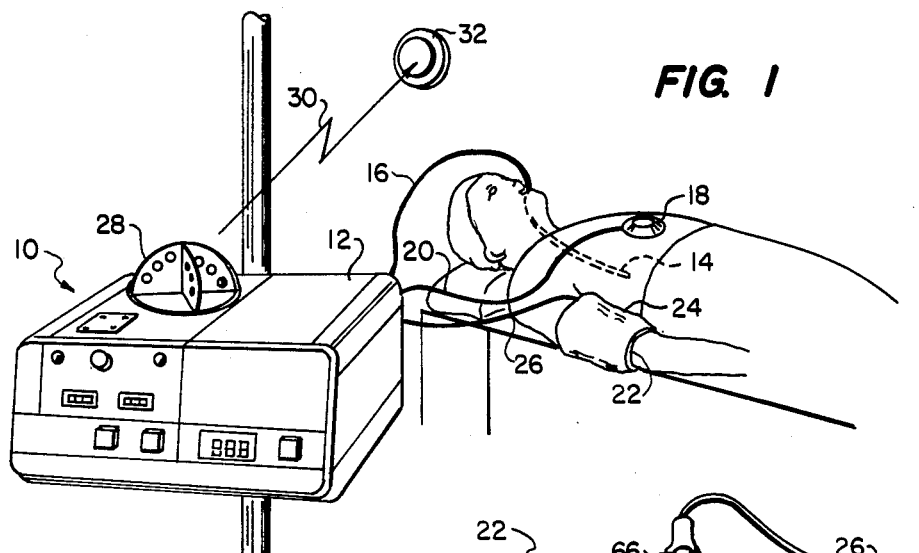
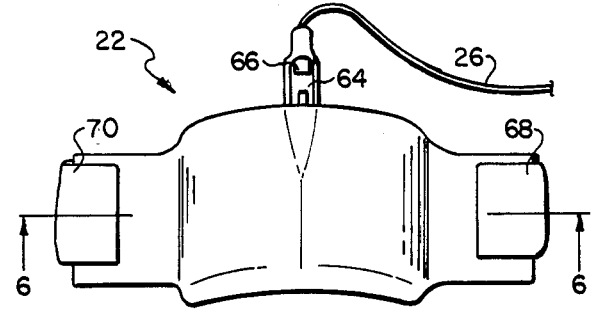
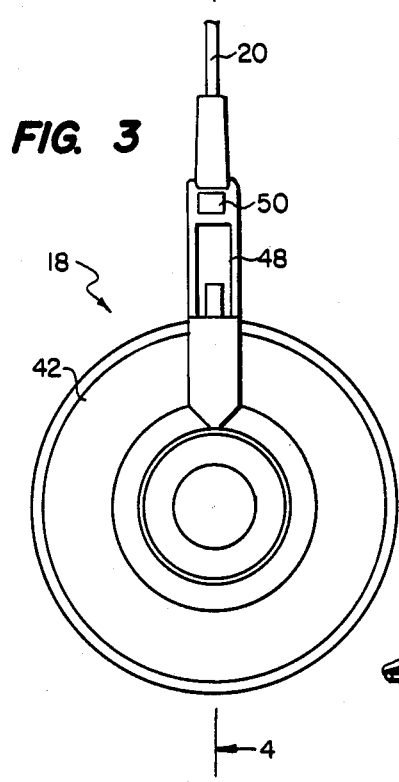
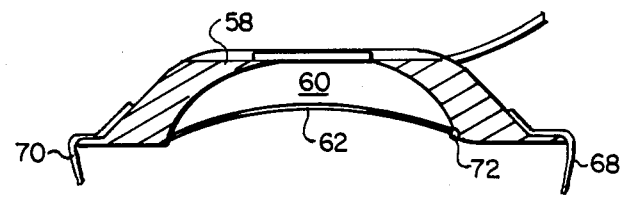
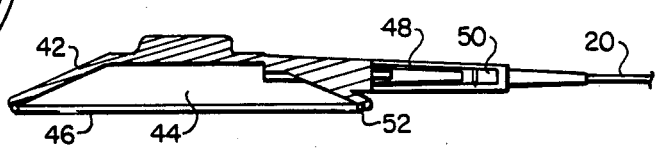

VITAL SIGNS MONITORING SYSTEM

This is a continuation of application Ser. No. 660,454, filed Oct. 12, 1984 (now abandoned), which was a continuation-in-part of application Ser. No. 522,640, filed Aug. 11, 1983, now U.S. Pat. No. 4,619,268, dated Oct. 28, 1986.

BACKGROUND OF THE INVENTION

The present invention relates patient vital signs monitoring systems and pertains particularly to an improved multi-mode system with a freely portable monitoring unit.

In the aforementioned application of which I am coinventor, a vital signs monitoring system is disclosed which includes an esophageal stethoscope catheter incorporating a miniature microphone for electrical pick up and transmission of signals representative of the sounds generated within the chest of a patient. These sounds of particular interest include the breathing sounds and the heart sounds. Processing circuits enable separation of the breath and heart sounds as desired by the operator and enable measurement of heart or pulse and breath or respiration rates and comparison of these measured rates with preset reference rates with means for initiating a visual or audible alarm in response to critical variations from the norm. The system includes temperature sensing means in the esophageal catheter and a processing system for processing the various signals with an IR transmitter and receiver combination with the transmitter transmitting the vital signs sounds by way of IR waves to a miniature portable receiver, including an earphone carried by a monitoring physician or anesthesiologist. This permits maximum mobility of the anesthesiologist with full monitoring capability during medical procedures while the esophageal stethoscope is in position.

During the critical times prior to and subsequent to insertion of the esophageal stethoscope into the patient, vital signs are normally monitored by an air tube stethoscope which monitors the heart and breath sounds or the blood flow sounds during measurement of blood pressure. This procedure however unduly ties the anesthesiologist to the patient during this critical monitoring period or in the alternative leaves the patient unmonitored during brief moments when the anesthesiologist must attend to other matters within an operating room.

It is therefore desirable that a vital signs monitoring system be available which permits a monitoring physician to constantly monitor the vital signs of a patient with full freedom to move about an operating room.

SUMMARY AND OBJECTS OF THE INVENTION

It is the primary object of the present invention to provide an improved vital signs monitoring system for a living being.

In accordance with the primary aspect of the present invention, a vital signs monitoring system includes an electronic precordial chest piece sensor and a blood pressure Korotkoff sounds audio sensor placed under the blood pressure cuff with these sensors connected to a control system for selectively sending the sensed signals by way of an IR transmitter to a miniature IR receiver to enable an attending physician to selectively monitor the respective sounds.

Another aspect of the invention includes the combination of a system which includes an esophageal stethoscope with a sound and temperature processing system with display and alarm systems for the signs. A selector switching arrangement enables the monitoring physician to select a selected one of the chest microphone, the blood pressure sounds sensor or the esophageal sensor.

BRIEF DESCRIPTION OF THE DRAWINGS

The above and other objects and advantages of the present invention will become apparent from the following description when read in conjunction with the drawings wherein:

FIG. 1 is a perspective view showing the system in position for operation;

FIG. 3 is a top plan view of a chest mounted sensing unit;

FIG. 4 is a sectional view taken generally on line 4—4 of FIG. 3;

FIG. 5 is a top plan view of an electronic blood pressure sensing unit; and

FIG. 6 is a section view taken generally on line 6—6 of FIG. 5.

Figure 2:
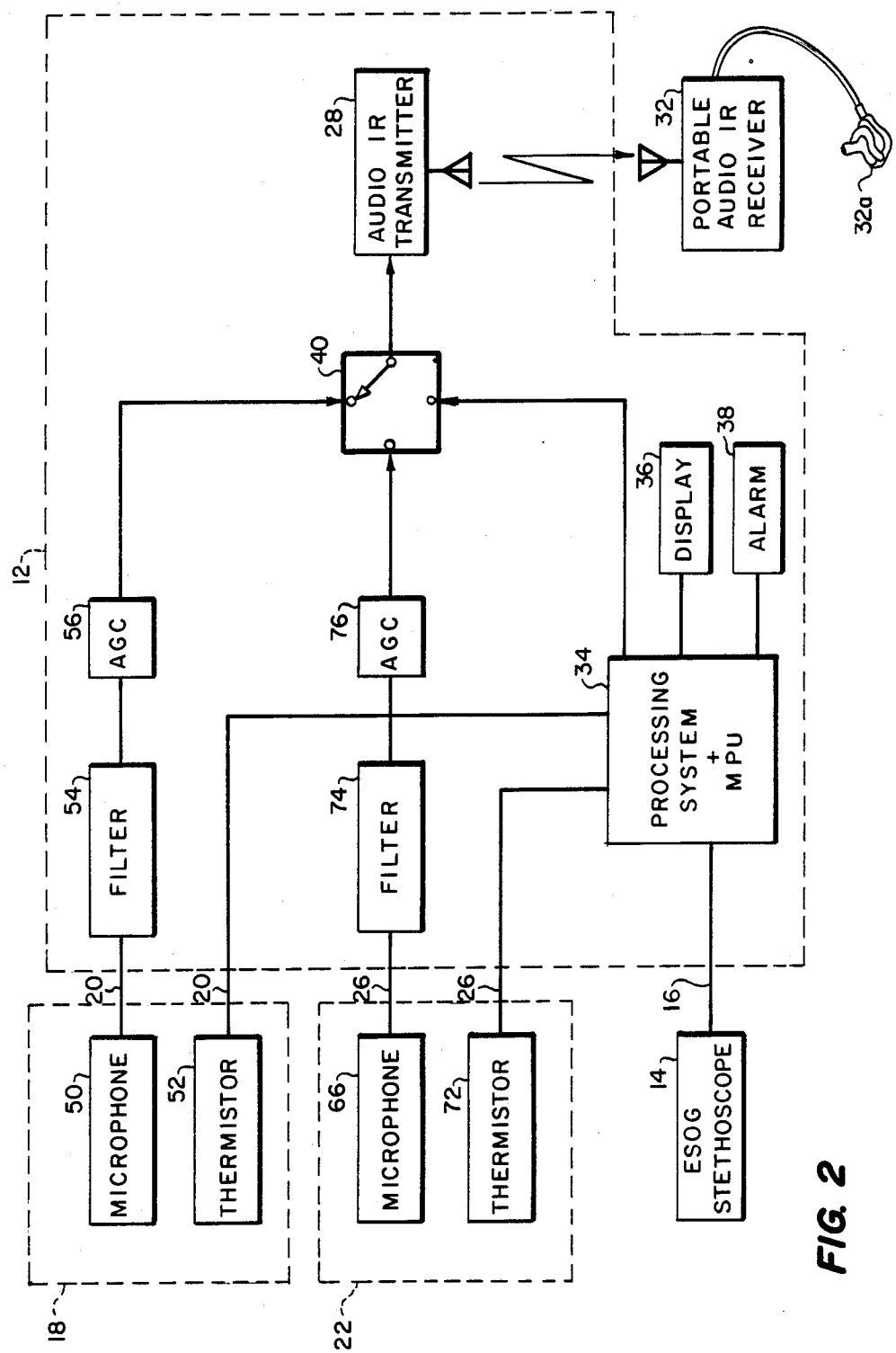
FIG. 2 is a schematic electronic block diagram for the system.

Referring to the drawings and primarily to FIG. 1, a monitoring system in accordance with the invention is illustrated as applied to a patient. The monitoring system comprises generally a monitoring unit designated generally by the numeral 10 which comprises a housing, the main control system, including a microprocessor unit, the basic electronics for the system, the various display and alarm devices and the IR transmitter.

The sensing modules or units comprise first an electronic esophageal stethoscope 14, connected by electrical leads 16 to the control unit 12. An electronic precordial chest sensor 18 is mounted on the patient's chest and is connected by electrical leads 20 to the control unit 12. An electronic blood pressure sounds sensor 22 is mounted over the brachial artery and secured in place under a blood pressure cuff 24 and is connected by electrical leads 26 to the control unit 12.

The control unit 12 includes the various signal processing and indicating systems and includes an infrared sound transmitter with an omnidirectional infrared emitter 28 which transmits an IR signal 30 to a miniature portable receiver 32 for monitoring by a monitoring physician by means of a suitable earphone or the like. As illustrated in FIG. 1, the infrared emitter or antenna 28 comprises a hemispherical transparent lens covering a plurality of quarter circle panels extending upright from a circular base and positioned around a vertical axis at about right angles to adjacent panels. A plurality of light emitting diodes are mounted on the face of each panel. This array of light emitting diodes provides for an omnidirectional transmission of infrared radiation.

Referring now to FIG. 2 of the drawing, a schematic electronic diagram of the system is illustrated. The system comprises a basic electronic vital signs monitor with a basic control system 12 which houses the basic signal and data processing components with the various sensors 14, 18 and 22 being interfaced with the control system unit by means of plug in cords or cables.

The esophageal stethoscope 14, as disclosed in the parent application, also includes temperature sensing means and a series of filters and amplifiers in the processing unit 12 which filter and enhance the signals sensed and processes the data through a processing system 34 which includes a microprocessing unit including ROM and RAM memory and the appropriate software programming to monitor the vital functions through the esophageal sensor and activate the appropriate displays 36 and alarms 38. Certain sounds are selected by a suitable switch arrangement 40 to an audio IR transmitter which transmits a signal 30 to a portable audio IR receiver carried by a monitoring physician with a suitable earphone or the like for monitoring the sounds. This basic system is covered in more detail in the prior application which is incorporated herein by reference.

The present system adds external sensing components to the system to enable monitoring of the patient's vital signs before the esophageal tube is inserted and connected and during any interruption in the monitoring through the esophageal sensor as well as subsequent to removal of the esophageal tube sensor system.

Referring now to FIGS. 3 and 4, an electronic precordial chest sensor 18, which comprises a generally frusto conical shaped cup or housing 42 is illustrated. The housing is preferably made of a sheet metal or hard plastic material defining an acoustic chamber 44 which is covered by a thin acoustic diaphragm 46 which contacts the chest surface of a patient. A tube 48 of the housing communicates with the acoustic chamber and houses an electronic microphone 50 which is connected by the cord 20 to the monitoring system. The sensor unit 18 also preferably includes a temperature sensing device 52 such as a thermistor which is connected by electrical leads to the processing system 34 as can be seen in FIG. 2.

The electronic precordial chest sensor 18 is attached to the patient's chest by an adhesive tape or the like and connected into the monitoring system such that the breath and heart sounds of the patient can be monitored during periods when the esophageal stethoscope is not in place or when it is desirable to interrupt use of the same. The chest and heart sounds are constantly monitored by a physician, particularly an anethesiologist, preparatory to surgery, during surgery, and following surgery. The anethesiologist is trained to interpret the sounds and any variations in the sounds to evaluate the condition of the patient during these periods.

The sounds picked up by the precordial sensor or microphone are transmitted in the form of electrical pulses from the microphone and are processed through a filter 52 such as a bandpass filter for filtering out background noises and the like. The signals are also processed through a suitable amplifier and automatic gain control 54 to further enhance the signals. The signals are then selectively transmitted by the audio IR transmitter to the physician by way of the portable audio receiver 32. The switch array 40 enables the physician to selectively monitor the precordial chest sensor, the blood pressure sounds sensor or the esophageal stethoscope.

Referring to FIGS. 5 and 6, the electronic blood pressure Korotkoff sounds pick up unit 22 is illustrated. The blood flow sounds sensor comprises a generally rectangular cup shaped housing 58 preferably formed of a somewhat resilient plastic or rubber curved down on the sides and ends forming a cup shaped housing defining an acoustic chamber 60. An acoustic diaphragm 62 covers the open side of the housing and the acoustic chamber 60. The diaphragm is designed to engage the surface over the artery inside the elbow of the patient for picking up the sounds of the blood flowing during pressure check. These sounds are commonly known as Korotkoff sounds, named after the discoverer thereof. These sounds during the blood pressure check by the physician are interpreted by him to provide an indication of the condition of the patient. A tube 64 communicates with the chamber 60 and contains an electronic microphone 66 which is connected by suitable electrical leads contained in the cord 26 to the monitoring system. Suitable Velcro or the like straps 68 and 70 are attached to and extend from the sides of the housing 58 for attachment around the arm of a patient.

This blood sound sensing unit 22 is placed on the arm inside the elbow over the brachial artery and is covered by a blood pressure cuff 24 during blood pressure check. A blood pressure cuff is an inflatable bladder that is typically attached around the arm such that, when inflated, it acts as a tourniquet closing off the flow of blood in the arteries. As the pressure is reduced in the cuff, the blood begins to flow through the artery making distinctive sounds which are monitored by a physician to enable him to evaluate the condition of the patient. A temperature sensing device or unit such as a thermistor 72 is also preferably carried by the sensing unit 22 and engages the surface of the skin for sensing the external temperature of the patient. The signals from the thermistor are transmitted by suitable electrical conductor to the processing system for processing in the usual fashion for comparison and display as desired.

The sounds picked up by the microphone 66 are transmitted by suitable electrical leads through the cord 26 to the processing and control unit wherein the signals are filtered through a filter system or circuit 74 such as a bandpass filter or the like and thereafter amplified and controlled through automatic gain control unit 76 before being transmitted by way of the switch array and the audio IR transmitter to the monitoring physician by way of his miniature portable receiver 32.

The above described system provides an elaborate system of simple and effective components that enables a physician such as an anesthesiologist to monitor the condition of a patient from a period prior to the administering of anesthesia and prior to the insertion of the esophageal stethoscope and the like, during and administering of anesthesiology, during surgery, and subsequent to surgery. The system also gives the monitoring physician complete freedom to move about an operating room without being tethered to the patient's monitoring system by means of conventional air column tubes as in the prior art devices.

In operation, a complete system as disclosed herein is readied in an operating room or preparatory room with the components thereof including the esophageal stethoscope, an electronic precordial chest sensor unit and an electronic blood pressure Korotkoff sounds sensor unit. The electronic precordial chest sensor and the electronic blood pressure sounds sensor unit may be attached immediately to the patient and connected to the vital signs monitor and control unit. The unit may be turned on blood pressure and chest sounds immediately monitored selectively prior to the insertion of the electronic esophageal stethoscope. The attending physician merely mounts the IR radio receiver which in the preferred embodiment comprises a unit approximating the size of a cigarette pack with volume control and an earphone attached. The physician simply places the receiver unit in a pocket or clips it to his coat and inserts the earplug or ear piece in his ear for listening. The physician may then selectively monitor either one of the chest sounds or the blood pressure sounds during the period prior to insertion of the esophageal stethoscope. Typically, anesthetic is administered prior to the insertion of the esophageal stethoscope, thus creating a critical monitoring period. After the esophageal stethoscope is inserted and attached to the vital signs monitoring and control unit, the stethoscope may be selected for monitoring by the physician. The internal chest and heart sounds, as well as internal temperature, are then monitored with the physician in constant receipt of the sounds of the heart and breath of the patient.

At any time during the procedure, the physician may selectively switch to either the monitoring or sensor units for monitoring the various sounds as well as monitoring the internal and external temperature through the temperature sensing elements. Differences between internal and external temperature can be easily and quickly monitored which also gives the physician an indication of the condition of the patient.

The present system is described in sufficient detail to enable one of ordinary skill in the relevant art to practice the invention. Many of the separate components which are not described in detail herein are state of art. For example, suitable microprocessing units are available from Intel Corporation as an 8085 and equivalent units are available from National Semiconductor Corporation.

While I have illustrated and described my invention by means of a specific embodiment, it is to be understood that numerous changes and modifications may be made therein without departing from the spirit and scope of the invention as defined in the appended claims.

I claim:

1. A portable patient vital signs monitoring system comprising, in combination:
   first sound sensing means to be attached to a patient's body for sensing heart and lung sounds and for generating a first electrical signal corresponding thereto;
   second sound sensing means to be attached to a patient's body for sensing blood flow and for generating a second electrical signal corresponding thereto;
   conductor means connected to said first and second sensing means for conducting said signals away from the patient's body;
   a remotely located monitoring unit including control means connected to said conductor means for receiving said first and second signals from said conductor means and for processing said signals;
   said monitoring unit including an IR transmitter having emitter means for omnidirectional transmission of said processed first and second signals; and
   a remote portable, IR receiver to be worn on an operator's body for receiving said processed first and second signals and for converting said received signals into audible form.

2. A monitoring system according to claim 1 wherein second sound sensing means comprises flexible housing means defining a sound chamber having a microphone therein for placement in engagement with a surface of skin of a body over a vein for sensing blood flow sounds when blood flow is restricted in said vein.

3. A monitoring system according to claim 2 wherein said flexible housing means comprises a generally rectangular cupped housing member defining said sound chamber having an open end; and
   an acoustic diaphragm covering the open end of said housing for engagement with said skin for sensing blood flow sounds in said vein.

4. A monitoring system according to claim 1 wherein said first sound sensing means comprises sound chamber means for mounting on the chest of a patient and a microphone disposed in said chamber.

5. A monitoring system according to claim 4 wherein said sound chamber means is defined by a housing having an open end; and
   an acoustic diaphragm covering said open end.

6. A monitoring system according to claim 5 wherein said housing has a generally frusto conical shape with a height to diameter ratio of less than one.

7. A monitoring system according to claim 6 wherein said housing includes strap means for attachment to an arm.

8. A monitoring system according to claim 7 wherein said housing is cooperative in combination with an inflatable blood pressure cuff and is positionable under and engageable by said cuff for sensing said blood flow sounds in a vein when the vein is restricted by the inflatable blood pressure cuff.

9. A monitoring system according to claim 8, including a thermistor mounted along the peripheral edge of said housing for engagement with a patient's body for sensing the external temperature of a patient; and
   said monitoring unit including means for monitoring the temperatuare sensed by the thermistor.

10. A monitoring system according to claim 6 wherein:
    said housing includes a thermistor mounted on the periphery thereof for sensing the external temperature of a patient; and
    said monitoring unit including means for monitoring temperature.

11. A vital signs monitoring system according to claim 10 wherein:
    said second sound sensing means comprises a generally rectangular elastic housing means having an open side; and
    an acoustic diaphragm covering said open side for mounting on an arm in contact with a skin area over a brachial artery and a microphone communicating with said chamber for sensing said blood pressure sounds.

12. A monitoring system according to claim 11 further comprising an esophageal stethoscope having means for sensing vital signs, and said monitoring unit including display means responsive to vital signs sensed by said stethoscope for displaying visual means indicative of vital signs sensed by said stethoscope.

* * * * *